(12) United States Patent
Pedrazzini

(10) Patent No.: US 8,852,507 B2
(45) Date of Patent: Oct. 7, 2014

(54) INTERFACING APPARATUS BETWEEN A PNEUMATIC MAIL SYSTEM AND A FEEDING SYSTEM OF BIOLOGICAL PRODUCT CONTAINERS TO A LABORATORY AUTOMATION SYSTEM

(75) Inventor: Gianandrea Pedrazzini, Paradiso (CH)

(73) Assignee: Inpeco Holding Ltd., Vallette (MT)

(*) Notice: Subject to any disclaimer, the term of this patent is extended or adjusted under 35 U.S.C. 154(b) by 0 days.

(21) Appl. No.: 13/985,391

(22) PCT Filed: Feb. 13, 2012

(86) PCT No.: PCT/EP2012/052384
§ 371 (c)(1),
(2), (4) Date: Aug. 14, 2013

(87) PCT Pub. No.: WO2012/110444
PCT Pub. Date: Aug. 23, 2012

(65) Prior Publication Data
US 2013/0322992 A1 Dec. 5, 2013

(30) Foreign Application Priority Data

Feb. 16, 2011 (IT) .............................. MI2011A0226

(51) Int. Cl.
*G01N 21/00* (2006.01)
*G01N 35/04* (2006.01)

(52) U.S. Cl.
CPC ........ *G01N 35/04* (2013.01); *G01N 2035/0481* (2013.01)
USPC .............. 422/63; 700/230; 700/245; 422/64; 422/65; 422/66; 422/67; 436/180

(58) Field of Classification Search
USPC ................ 700/230, 245; 422/64–67; 436/180
See application file for complete search history.

(56) References Cited

U.S. PATENT DOCUMENTS

| 3,907,231 | A | 9/1975 | Kreiner |
| 4,395,164 | A | 7/1983 | Beltrop et al. |
| 4,526,045 | A | 7/1985 | Reekie |
| 2010/0312379 | A1 | 12/2010 | Pedrazzini |
| 2011/0002760 | A1 | 1/2011 | Pedrazzini |

FOREIGN PATENT DOCUMENTS

| EP | 0516111 A1 | 12/1992 |
| GB | 1323530 A | 7/1973 |
| WO | 2009/068574 A1 | 6/2009 |
| WO | 2009/092710 A1 | 7/2009 |
| WO | 2010/003880 A1 | 1/2010 |

*Primary Examiner* — Jyoti Nagpaul
(74) *Attorney, Agent, or Firm* — Jacobson Holman, PLLC

(57) ABSTRACT

An interface apparatus between a pneumatic mail system and a feeding system of biological products to a laboratory automation system is described, the apparatus comprising a capsule suitable for being conveyed in a pneumatic mail system which accommodates therein one or more biological material containers, said capsule opening and connecting to a device for transferring said biological material containers contained in said capsule into at least one recruiting device of said biological product containers, said at least one recruiting device being used to load said containers of biological products into a positioning device interfaced with a gripping device of said biological product container for transferring said biological product container on an automatic conveyor belonging to a laboratory automation system. Said capsule has an inner chamber containing foam elements adapted to withhold said biological product containers present in said capsule.

7 Claims, 9 Drawing Sheets

INTERFACING APPARATUS BETWEEN A PNEUMATIC MAIL SYSTEM AND A FEEDING SYSTEM OF BIOLOGICAL PRODUCT CONTAINERS TO A LABORATORY AUTOMATION SYSTEM

This is a national stage of PCT/EP12/052384 filed Feb. 13, 2012 and published in English, which has a priority of Italian no. MI2011A000226 filed Feb. 16, 2011, hereby incorporated by reference.

The present intervention concerns an interfacing apparatus between a pneumatic mail system and a feeding system of biological product containers to a laboratory automation system.

Nowadays, the problem of transporting biological product specimens in hospital departments, in particular from the point in which such specimens are drawn from the patient to the various stations in which the concerned specimens must be tested, is an increasingly critical problem and spurs to seek increasingly more practical, faster solutions for optimizing such a process.

In particular, it is necessary to interface the systems which transport the specimens drawn from the patient, enclosed in appropriate containers, with devices intended to load the specimens themselves onto a laboratory automation system, from which, by means of appropriate conveyor belts, the specimens are routed to the various stations or test modules present in the laboratory.

An apparatus which loads the biological product containers in fully automated manner onto the conveyor belts must be used for interfacing.

With this regards, a known system, particularly used over the past years for the purpose of transporting biological product containers, consists of a pneumatic mail system, which besides is used also in areas other than medical; in particular, it is a mechanism for delivering biological product containers, possibility inserted one by one or in groups in plastic casings and enclosed in larger containers, or capsules, generally of cylindrical shape, which travel supported by compressed air in a tube network to finally reach an arrival station, where the capsule opens and makes the specimens available so that they can be taken and possibly transferred, as mentioned, to a laboratory automation system. The system then requires the capsule, once emptied, to close and start off again along the tube network (to return, for example, to a point in which it may be filled again with new biological product containers), and in the same manner a new full capsule to reach the arrival station to be emptied. To this effect, the Applicant has previously filed a patent (PCT/EP2008/066262) which describes the totally automated interfacing of a pneumatic mail system, which transports biological product containers, with the Applicant's laboratory automation system. In the latter patent, in order to take the biological product containers from the capsule once opened, by means of automated gripping devices, and transfer them to the laboratory automaton system it naturally derives that the biological product containers cannot be inserted in plastic casings; in this manner, the aforesaid transfer process is speeded up, with respect to the known systems which require the presence of an operator who manually opens the casing and extracts the biological product containers inserted therein.

However, problems in the use of such an interfacing apparatus appear.

Indeed, the biological product containers travel inside capsules, intended to move along the pneumatic mail system, inserted, in turn, in particularly large, heavy containers (carriers), which normally have only a predetermined number of available holes for accommodating the test tubes.

Thus, interfacing with the laboratory automation system implies that both the single biological material containers and the heavy carriers, once filled or emptied of the containers themselves, must be moved by means of gripping devices. The solution of the previous patent includes the use of two separate containers and/or carrier gripping devices, one for those arriving from the pneumatic mail system and one for those to be sent to the system itself.

Furthermore, such carriers have a polygonal shape due their build, and therefore the apparatus must include orientation devices for the carrier to be appropriately oriented to be inserted in the capsule.

What is more, it is fundamental for the capsule traveling along the pneumatic mail system to always maintain the appropriate orientation, i.e. it must not turn up the interface with one of the gripping devices; this particularly applies to the step of unloading of the biological product containers, obviously because in this case the gripping device would not be able to grasp the single biological material containers after the capsule has opened because the carrier is upside-down.

Furthermore, even if the carrier is dimensioned to perfectly fit in the capsule, the biological material containers are inserted in holes obtained in the carrier; consequently, they are, however slightly, distanced apart and therefore the sealing during transport is not entirely perfect.

In general, the presence of the carriers reduces the actual area which can be occupied by the biological material containers within the capsule, in addition to making it particularly heavy and thus transportable with greater difficulty in the compressed air tubes of the pneumatic mail system.

Furthermore, a system like this does not take the processing priority of some specimens over others into account, this being a situation which may very often occur in a test laboratory when some specimens need to be tested more urgently than others, e.g. because they have been drawn from patients who have just been visited in an emergency department and who therefore require immediate testing and care.

As apparent, the concerned interfacing apparatus displays some problems related to the low efficiency of the performed operations and to the high cost for making the used apparatuses.

It is the purpose of the present invention to make an apparatus which allows to insert a higher number of biological product containers within each capsule, ensuring the perfect sealing of the containers themselves within the capsule, and to speed up the loading operations of such containers in the laboratory automation system, so that, despite the higher number of containers present therein, the capsule is lighter and thus moves faster along the pneumatic mail system tubes.

Another object of the invention is to ensure a separate management of biological product specimens to be processed with urgency with respect to the ordinary ones.

A yet further object of the invention is that of being able to disregard the orientation of the capsule coming from the pneumatic mail system and thus of the biological containers contained therein, the sense in which said containers are made available to the system intended for loading them into the laboratory automation system being irrelevant.

A not last object is to make an apparatus which has high efficiency and low manufacturing costs.

This and other objects are reached by an interfacing apparatus as described in claim 1.

These and other features of the present invention will be further apparent from the following detailed description of an example of embodiment thereof, shown by way of non-limitative example in the accompanying drawings, in which.

Figure 1:
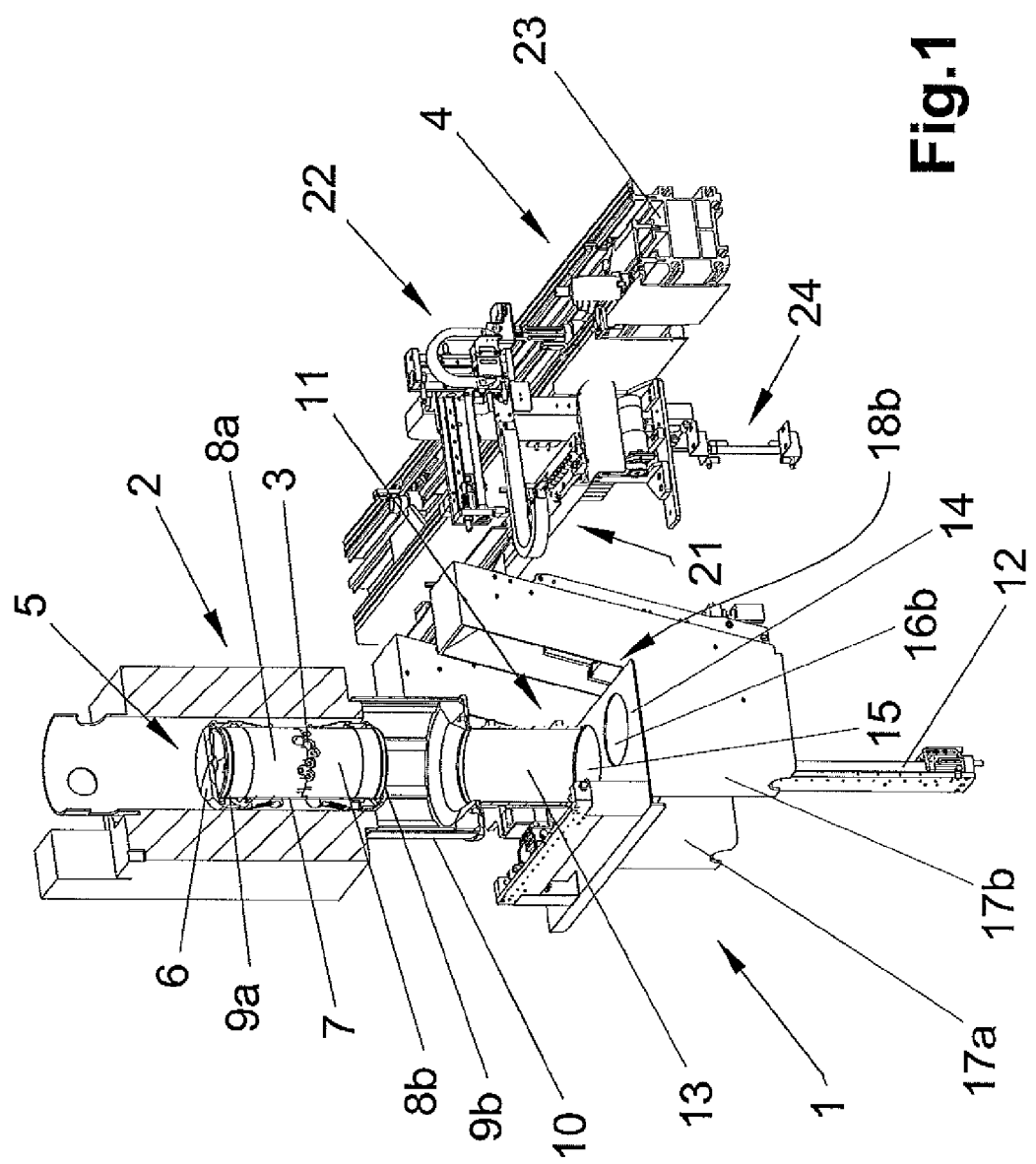
FIG. 1 shows a perspective, partially sectioned view of the interfacing apparatus according to the invention in the initial situation in which the capsule from the pneumatic mail system is about to arrive.

An interfacing apparatus 1 connects a pneumatic mail system 2 (of which only the end part of the conduit is shown), which transports biological product containers 3 drawn directly from patients in a hospital department to a feeding system of biological product containers to a laboratory automation system 4, which transports the containers themselves to different test stations or modules possibly connected thereto.

The biological product containers 3, for example test tubes, travel inside a capsule 5, which has an opening outer casing 6 and an inner chamber 7, preferably cylindrical, and which contains foam elements 8a and 8b, with a high elastic modulus, joined at the two ends of the inner chamber, where two closing flanges are found, one upper flange 9a and one lower flange 9b, which work as closing plug of the inner chamber 7.

A device 11 for transferring the test tubes 3 contained in the capsule 5 is present underneath the arrival station 10, which is open at the bottom, of the pneumatic mail system 2. This transfer device 11 comprises a piston 12 which moves vertically, adjusted by start and end limit stops, to engage the lower flange 9b of the inner capsule chamber 5, and a sliding tube 13 (shown in section in all figures), preferably cylindrical and open at the two upper and lower ends, which translates pneumatically for the purposes which will be described better below.

The lower edge of the sliding tube rests on a surface 14 which has three different cavities, one central cavity 15 of dimensions such as to allow the passage of the flange 9b and of the foam element 8b of the capsule 5, and two side cavities 16a and 16b, of possibly irregular shape, but of length equal to at least the diameter of the sliding tube 13.

Each of the two side cavities is connected to a compartment 17a and 17b underneath, particularly a hopper, in which a recruiting device 18a, 18b is accommodated, entirely similar to that described in another patent by the Applicant (PCT/EP2009/050597).

Similarly to that described in the latter patent, the recruiting devices 18a and 18b are intended, by means of a system of mobile combs 19 running on fixed combs 20, to load test tubes into a test tube positioning device 21, comprising one or more lanes, in order to be able to accommodate test tubes of different diameter.

The positioning device 21, by making the test tubes slide along such lanes, makes them available to a gripping device 22 which grasps the test tubes and transfers them into transport devices positioned on an automatic conveyor 23 of a laboratory automation system 4, i.e. a conveyor belt from which the test tubes are then transferred to the various stations or test modules present in the laboratory.

Operation is as follows: after having drawn a series of biological material for example from a given number of patients in a hospital department, an operator manually loads in random manner in a capsule 5 (opening it on the side of one of the flanges 9a and 9b and then closing it all) a given number of test tubes 3 containing the drawn biological material; such test tubes 3 were appropriately provided beforehand with barcodes to ensure the biological specimen-patient association, so that afterwards the automation system, by means of reading devices of the barcode of the test tube 3, already knows how to address each single test tube via a communication protocol with the Laboratory Information System (LIS), toward the appropriate test modules which each specimen requires. The application of the barcode on each single test tube occurs by means of a specific automatic test tube marking apparatus, e.g. that of patent PCT/EP2009/058360 by this Applicant.

Figure 2:
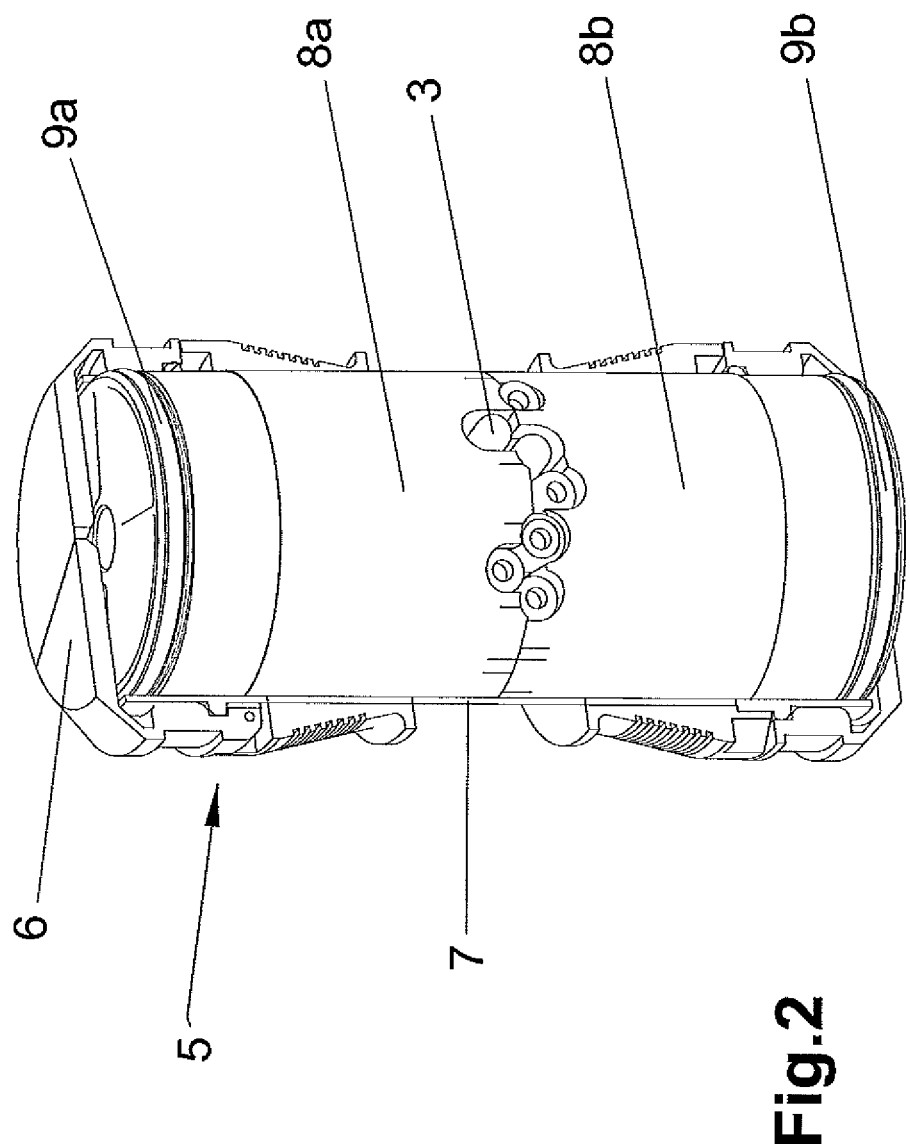
FIG. 2 shows in detail the biological material containers withheld inside the capsule (which is shown in section) by the foam elements.

In the capsule 5, the test tubes 3 are withheld in sealed manner by the foam elements 8a and 8b glued to the flanges 9a and 9b, as shown in FIG. 2; this occurs both for a minimum number of inserted test tubes 3, because even in an empty capsule 5 configuration the foam elements 8a and 8b nearly touch each other (and therefore their size is calibrated so as to withhold possibly even one only test tube in sealed manner) and in a configuration in which several tens of test tubes are inserted in the capsule 5.

In general, the entire transport system can be adapted to different sizes of the capsule 5 and of the foam elements 8a and 8b inside the capsules.

During transport, in the unfortunate case in which one of the test tubes 3 should undergo a shock and either open or break, the spilled biological material is absorbed by the foam elements, without being dispersed outside the capsule 5. The risk of contamination is thus minimal.

The capsule 5 is thus sent to the tube network of the pneumatic mail system 2 to reach near the arrival station 10, which is open underneath the mail system 2 (FIG. 1).

Figure 3:
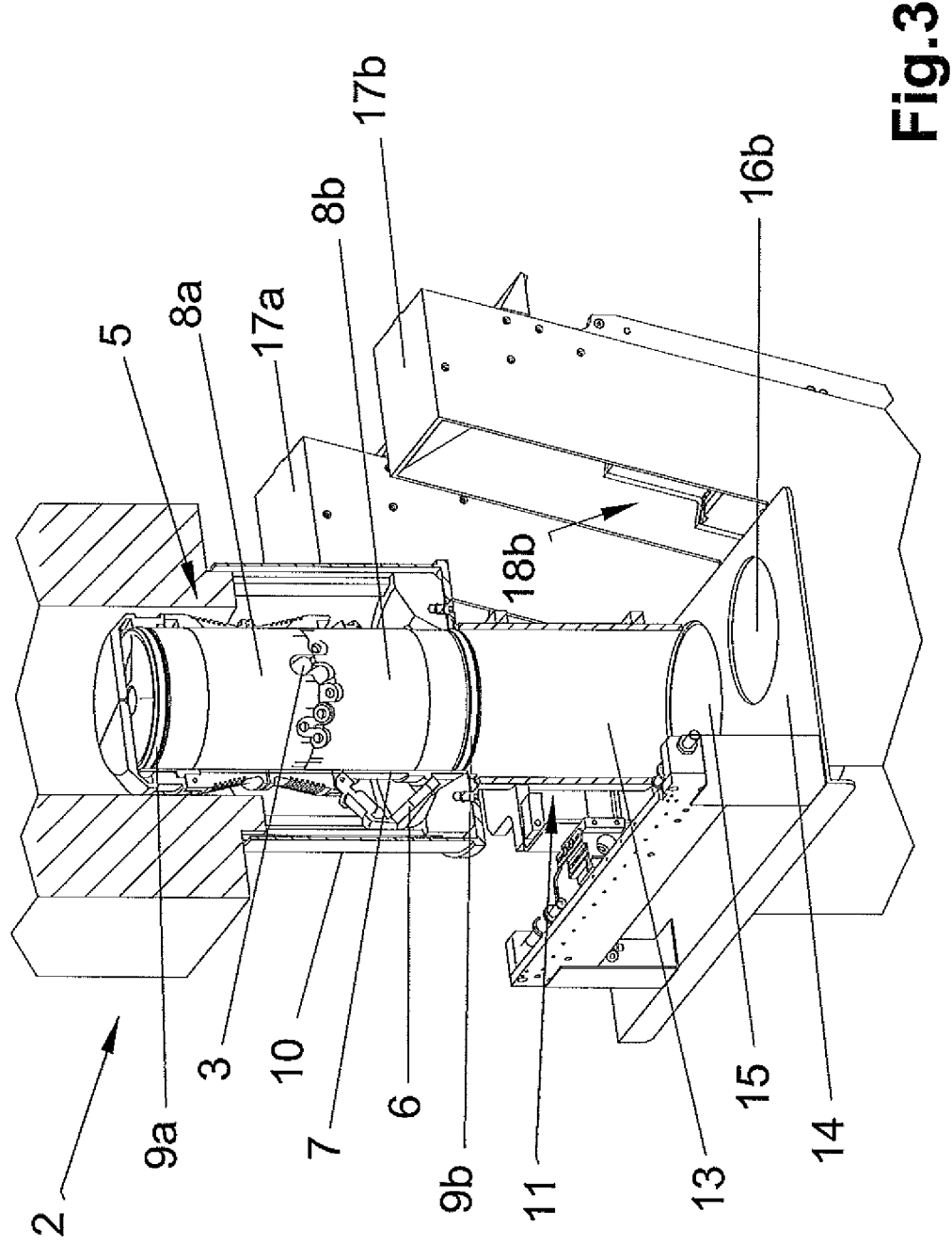
FIG. 3 shows in detail the opening of the capsule when it reaches the pneumatic mail system arrival station.
Figure 4:
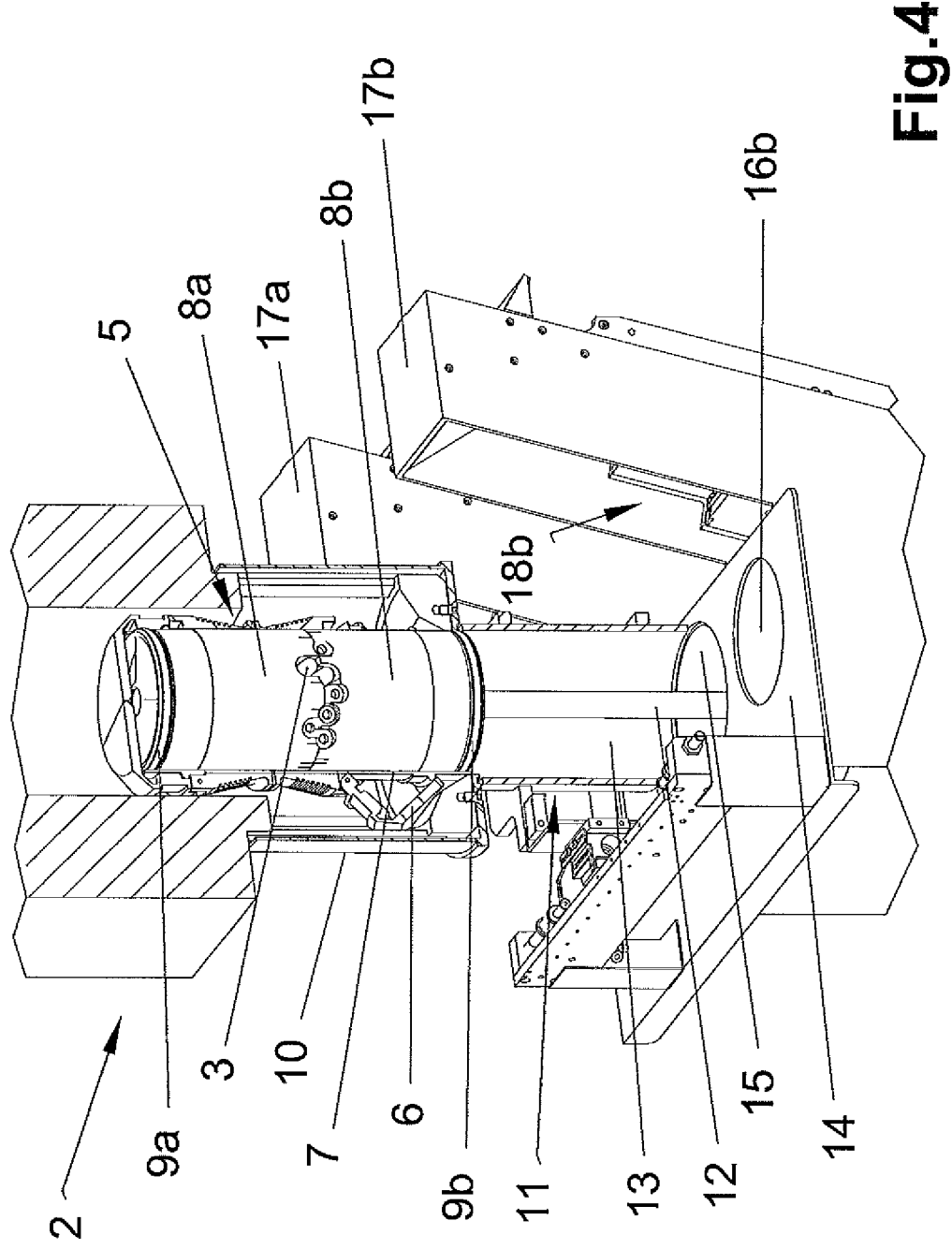
FIG. 4 shows in detail and in section the device for transferring the biological product containers in a first step of operation.

After the capsule 5 reaches the arrival station 10, the lower part of the outer casing 6 of the capsule 5 itself is opened automatically by a mechanical system (FIG. 3). At this point, the piston 12 is lifted pneumatically (FIG. 4) from the bottom through the central cavity 15 of the surface 14, along with the sliding tube 13, which in the resting position is located at the central cavity 15 itself, and engages the lower flange 9b of the inner chamber 7 of the capsule 5, then moving downward and consequently dragging the lower flange 9b, along with the lower foam element 8b glued thereto.

The movement of the piston 12, both upward and downward, is adjusted by start and end travel stop sensors, preferably sensors which can engage a slider integral with the piston, recognizing when the piston itself has reached the lower and higher point of its vertical movement, respectively.

Figure 5:
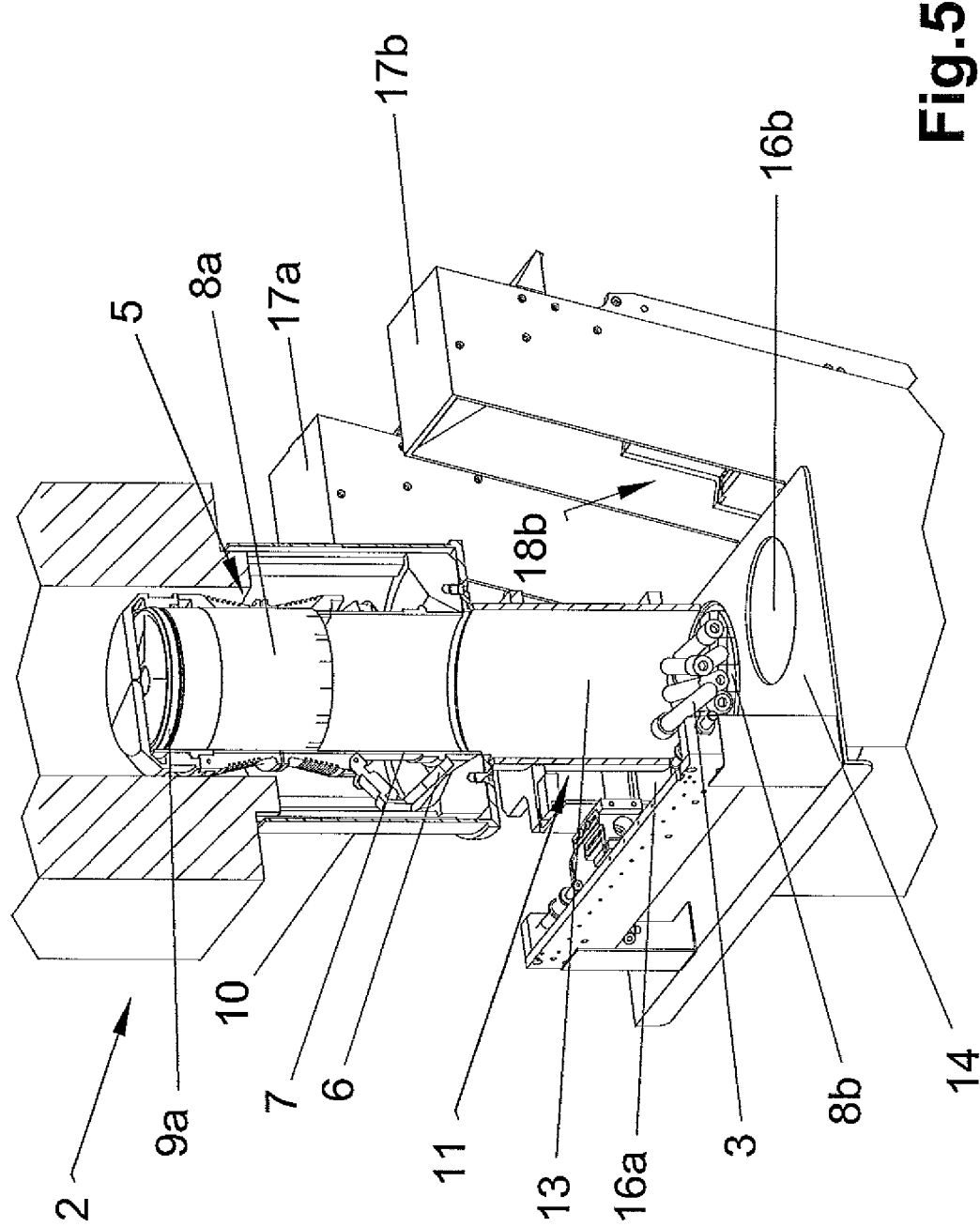
FIG. 5 shows in detail and in section the device for transferring the biological product containers in a second step of operation.
Figure 6:
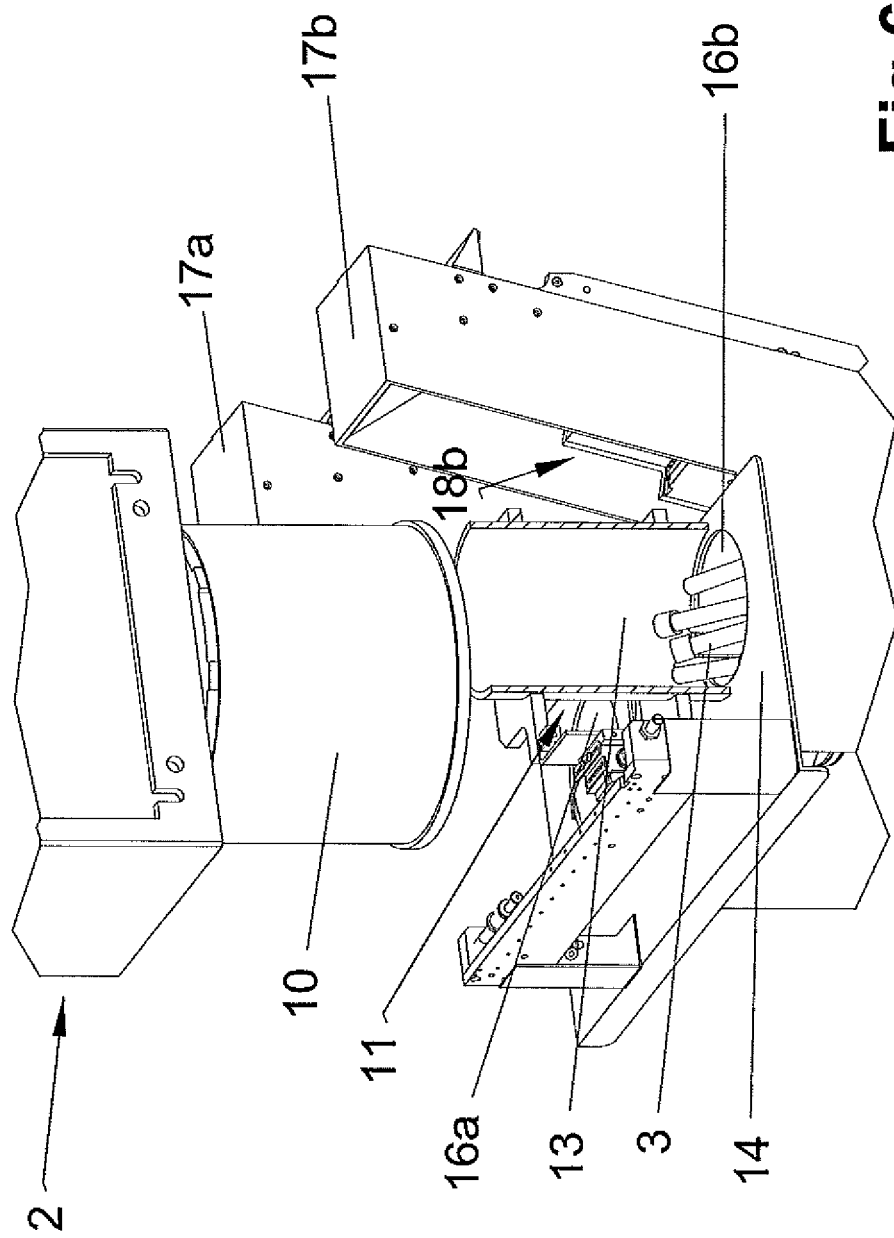
FIG. 6 shows in detail and in section the device for transferring the biological product containers in a third and last step of operation.

When the piston 12 goes back to the lower position (situation shown in FIG. 5), the upper part of the lower foam element 8b is precisely leveled with the surface 14 and the test tubes 3 are thus horizontally accommodated within the sliding tube 13, at this point the tube 13 moves pneumatically to one of the two side cavities 16a, 16b, into which it lets the test tubes 3 fall (FIG. 6).

One of the most innovative aspects of the invention is the possibility of separating the transfer of one of the test tubes into two separated cavities, according to whether the test tubes must be processed in ordinary manner or urgently. It is in all cases possible that only one cavity, and thus only one hopper and only one recruiting device, is present.

Obviously, the transfer of the test tubes into either one or the other hopper 17a or 17b is automatically managed by the interfacing apparatus 1 itself; indeed, in the moment in which the test tubes 3 are manually loaded by the operator into the capsule 5, the Laboratory Information System contains the information concerning whether the test tube is urgent or not being such test tubes 3 already provided with barcodes being registered in the system. As a consequence of this, when the sliding tube 13 comes into action it is automatically routed to shift to either one or the other of the side cavities 16a, 16b.

It is apparent that this solution implies that all the test tubes 3 traveling in the same capsule 5 are of the same type, either only ordinary or only urgent; however, a further embodiment (not described in the accompanying figures) may require ordinary and urgent test tubes 5 to be inserted in the same capsule 5, separated by a further central foam element; in this case, the piston 12 must first move the first group of test tubes which it encounters, with the capsule open, downwards and the sliding tube 13 must move them into one of the side cavities; subsequently, the piston 12 draws the central foam element 8c downwards, possibly also glued to a further central flange 9c, and the sliding tube 13 moves the other group of test tubes, which were initially positioned on the top of the capsule 5, into the other side cavity.

Figure 8:
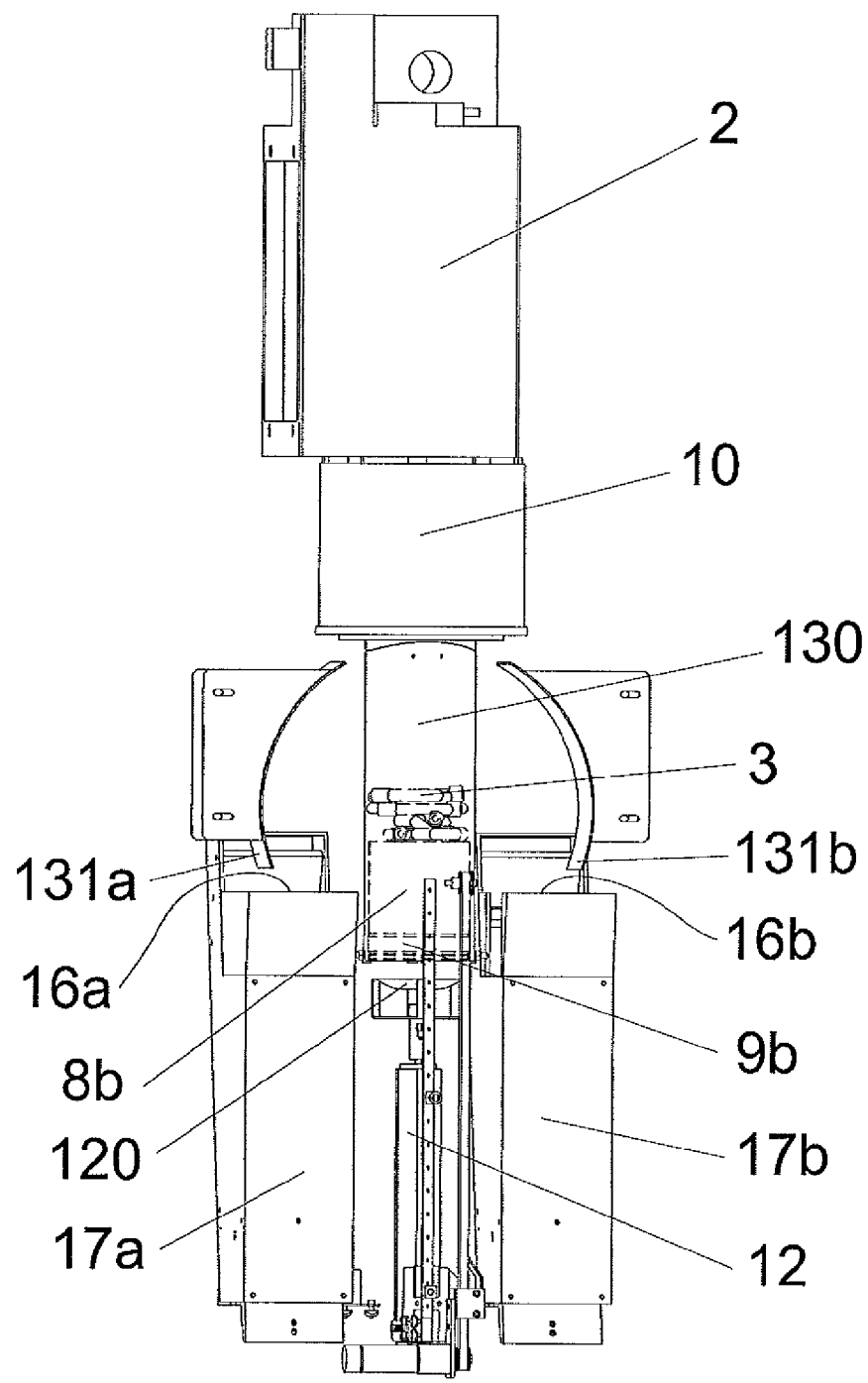
FIG. 8 shows again a detail of the device for transferring biological product containers in a second embodiment and in a first step of operation.

A second embodiment (shown in FIGS. 8 and 9) of the transfer device 11 comprises a tube 130, which no longer slides horizontally over the other of the two side cavities 16a, 16b, but is instead rotatable substantially by 135° in either one or the other direction with respect to resting direction, to unload the test tubes 3 into the cavity 16a or 16b, and thus into the respective hopper 17a or 17b (FIG. 9), from the top.

The lower flange 9b is engaged during the upward movement of the piston 12 (advantageously by means of a suction cap 120) and is thus pushed downwards along with the lower foam element 8b and the test tubes 3.

Subsequently, the suction cap 120 is disengaged from the lower flange 9b (FIG. 8) and the test tubes 3 are unloaded.

To make the rotatable tube 130 unloads test tubes into either one or the other of the cavities it is sufficient to reverse the sense of rotation of the motor used to actuate the tube 130.

Two arc-of-circumference-shaped partitions 131a, 131b are present to prevent the escape of test tubes 3 during the rotation of the tube 130. Obviously, such partitions are interrupted in the end part by the rotatable movement of the tube 130 to allow unloading of test tubes 4 in the cavity 16a, 16b.

Figure 9:
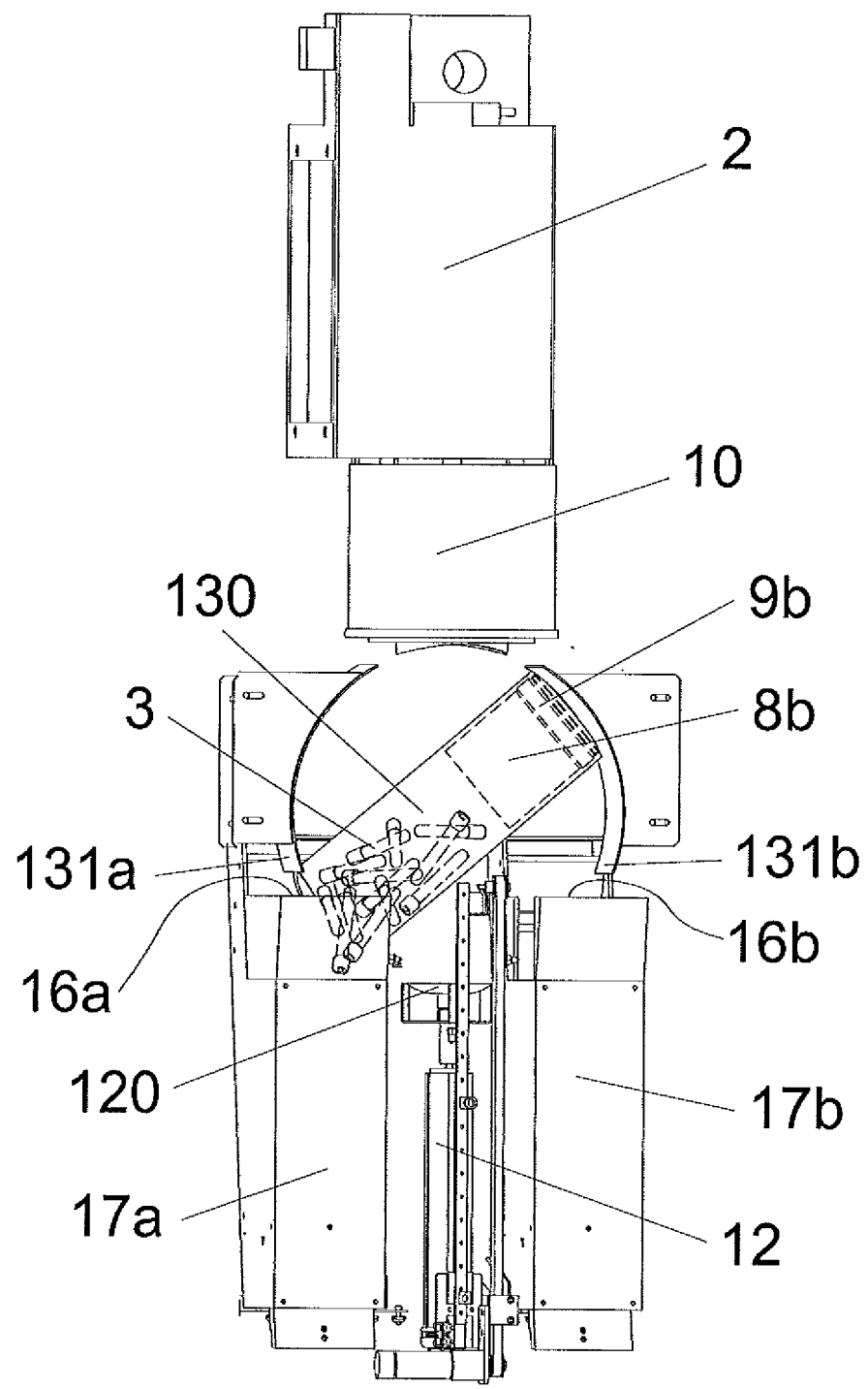
FIG. 9 shows the same detail of FIG. 8 in a second step of operation.

This second embodiment differs from the previous one in that the lower flange 9b, and consequently the lower foam element 8b glued thereto, remain integral with the walls of the rotatable tube 130, thus turning therewith (FIG. 9).

In all cases, the test tubes fall alternatively into either one or the other of the two side cavities 16a, 16b, and thus into the respective hopper 17a, 17b, and at such a drop it operates one or the other of the two recruiting devices 18a, 18b (obviously, the one inside the hopper into which the test tubes dropped) intended to supply test tubes to the positioning device 21, while the other remains still.

Once the transfer operation is complete, i.e. when the capsule 5 has been emptied, the piston 12 rises upwards, pushing with it the lower flange 9b still engaged thereto and the lower foam element 8b glued to the flange itself.

The lower flange 9b and the lower foam element 8b thus returns to their initial position in the capsule 5; at this point, the piston 12 is disengaged from the lower flange 8b, the piston 12 descends downwards again, and at the same time the capsule 5 closes and starts off again, from the arrival station 10, to the tube network of the pneumatic mail system 2, to return, for example, to a point in which it may be reopened again by an operator and filled with new specimens.

In this manner, the arrival station 10 is ready to accommodate a possible new full capsule.

The apparatus 1 can always ensure loading priority to test tubes to be processed urgently with respect to those to be processed in ordinary manner.

Figure 7:
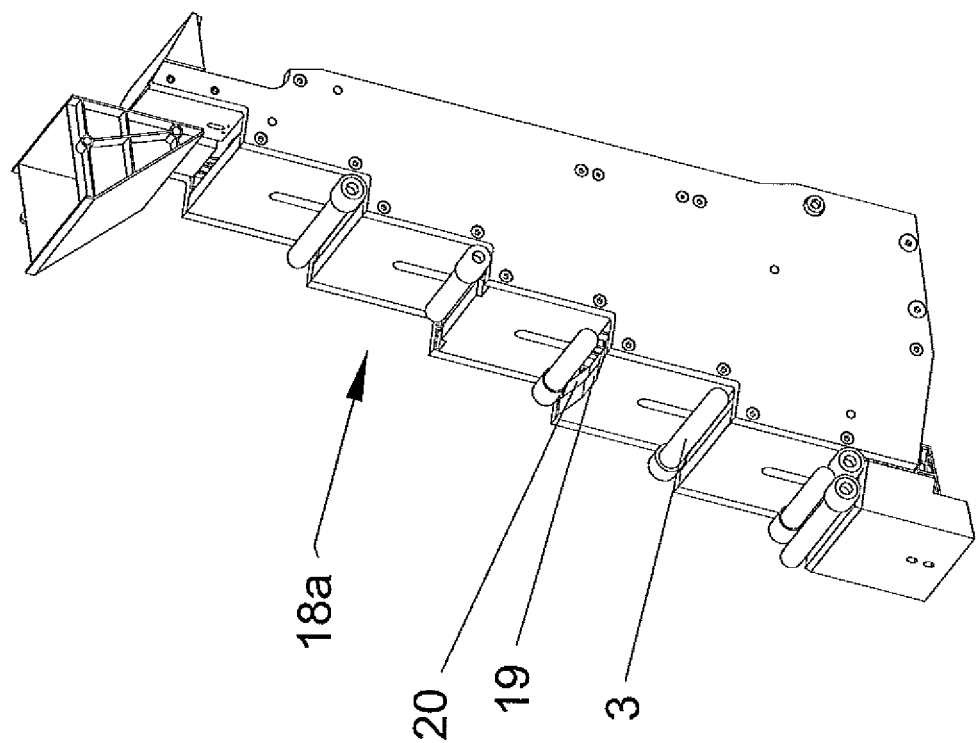
FIG. 7 shows in perspective view one of the two recruiting devices in action, having removed all the rest.

Indeed, if the situation occurs in which the recruiting device 18a dedicated (in the illustrated embodiment) to the ordinary test tubes is loading test tubes onto the positioning device 21, but at the same time the transfer device 11 is unloading new test tubes to be processed with urgency into the hopper 17b, recruiting device 18a immediately blocks giving priority to recruiting device 18b which must load urgent specimens. Once all the test tubes have fallen into the hopper and the respective recruiting device has started up, the test tubes are lifted by the mobile comb sliding system 19 onto the fixed combs 20 (FIG. 7), similarly to that described in patent PCT/EP2009/050597: it is thus worth noting that the orientation with which the test tubes 3 were originally loaded by the operator in the capsule 5 is not at all relevant. Indeed, once the test tube 3 drops and is then lifted by the recruiting device, considering the test tube itself laying on the mobile combs 19 of the recruiting device, it is absolutely indifferent whether it has, in frontal view, the cap facing either leftwards or rightwards. Indeed, in either case, once it reaches the top of the recruiting device it slides to the positioning device 21, performing a 90° rotation and remaining suspended and resting on the lane of the positioning device 21 by means of the plug, protruding with respect to the side body of the test tube 3.

Besides, the recruiting device as described in the aforesaid patent PCT/EP2009/050597 has already been studied with regards to the loading of test tubes 3 thrown in bulk into the hopper: the configuration may thus be reapplied for the purposes of the present invention.

The described embodiment implies that the test tubes 3 used all have the same diameter; in all cases, the apparatus 1 may also be capable of managing test tubes of different diameter. In this case, the positioning device 21 comprises (solution not shown in the accompanying figures) a pair of lanes of different width adapted for the positioning of test tubes of different diameter. In particular, being the near totality of test tubes containing biological products present on the market and used in test laboratories of the 13 mm diameter and of the 16 mm diameter type, a lane adapted to position test tubes of 13 mm of diameter and a lane adapted to position test tubes of 16 mm of diameter are needed.

In particular, the test tubes of 16 mm of diameter, initially falling onto the lane intended for positioning the 13 mm test tubes only, will remain in laying position because they are wider than the width of such a lane, and are thus conveyed, by means of a diverter, onto the appropriate lane adapted to position test tubes of different diameter.

It is worth specifying that in all cases the described device 21 may be adapted to positioning test tubes of any diameter, simply by appropriately dimensioning the lanes.

Therefore, the test tubes 3 divided according to the case onto the two lanes, reach an appropriate loading area where they are queued waiting to be grasped by the gripping device 22 and unloaded onto the conveyor 23 of the laboratory automation system 4, from where they are transported to further processing or testing modules interfacing with the conveyor itself.

Additionally, it is worth noting that the test tubes existing on the market and used in test laboratories, in addition to having different diameters may also have different heights, and so appropriately in the aforesaid loading area there should be a lifting device 24 with the purpose of lifting the test tubes so that the bottom of the test tube is always positioned at the same height, regardless of the height of the test tube itself. The need to have such a lifting device 24 is related to the fact that the gripping device 22 comprises a pneumatically actuated mechanical arm, which can grasp the test tubes, and reach all the points needed to preform the required operations but can in all cases always only reach the same height during all vertical movements.

In all cases, for a detailed description of all parts constituting the recruiting device 18a, 18b, the positioning 21 and the test tube gripping device 22, reference is made as mentioned to patent PCT/EP2009/050597 by the Applicant.

The filling procedure of capsules 5 to the apparatus 1 itself may be considerably accelerated if the apparatus 1 has a connection to two different conduits of the pneumatic mail system 2, one intended to accommodate the capsules 5 coming directly from the drawing area and thus containing the test tubes 3, and the other intended for the subsequent restarting of the emptied capsules 5, which must go back to the loading point to then be filled again. It is instead apparent that a connection to only one conduit implies that each time that a capsule 5 arrives and unloads the test tubes 2 to the interfacing apparatus 1, one must wait for the capsule 5 itself to leave the free conduit, before being able to accommodate the capsule itself. If instead at the end of the emptying operation the capsule 5 is diverted onto a separate return conduit, obviously the next capsule may reach the interfacing apparatus 1 more rapidly, and the test tube loading speed 3 onto the conveyor 23 will also increase as a consequence.

The innovative aspect of the invention is thus constituted in that, with respect to the interfacing apparatus, with a pneumatic mail system described in patent PCT/EP2008/066262, a single capsule contains a higher number of test tubes while being in all cases lighter and traveling faster in the tubes of the mail apparatus, given the absence of carriers inside.

Furthermore, the sealing of the test tubes in the capsule is absolutely perfect by virtue of the action of the foam elements, both in the ease in which the test tubes inserted in the capsule are a few units or if there are several tens of them because the foam elements have a very high elastic modulus and may be considerably compressed. What is more, in case of breakage or spillage of biological material from one of the test tubes, contamination is absorbed by the foam element themselves without being dispersed outside the capsule.

Furthermore, the orientation that the capsule presents to the interfacing apparatus with the loading system is irrelevant because in all cases the action of the piston consisting in coupling and dragging one of the two flanges and the foam end connected thereto regardless of which the two ends of the inner chamber of the capsule is presented in contact with the piston; instead, in the previous solutions, it is important to ensure that the capsule reaches the interfacing point with appropriate orientation to avoid that in its opening it presents the bottom side instead of the test tube side of the carrier.

Above all, the interfacing apparatus is designed to allow, through the presence of two hoppers and two separate recruiting devices in which the test tubes are alternately poured, the simultaneously management and the respective load on the laboratory automation system of the test tubes containing biological products to be tested in ordinary or urgent manner ensuring the loading priority of the latter at the same time.

It must further be considered the objective simplification of the test tube loading process on the conveyor of the laboratory automation system because there is only one gripping device which manages such a process, and no longer a pair of gripping devices as in the previous solutions.

It has been practically seen that the device as described may reach the predetermined objects ensuring faster and more efficient loading of test tubes on the laboratory automation system conveyor with respect to the known interfacing systems of a pneumatic mail system with a test tube feeding system to a laboratory automation system.

Furthermore, the apparatus is simplified also from the structural point of view allowing a reduction of the assembly and maintenance costs of the same.

The invention thus described is susceptible to many changes and variants, all comprised within the scope of the inventive concept.

In practice, the materials used as well as the shapes and size may be any, according to needs.

The invention claimed is:

1. An interfacing apparatus between a pneumatic mail system and a laboratory automation system, comprising a transfer device of biological product containers arriving from the pneumatic mail system inside capsules comprising an inner chamber, where said transfer device comprising a surface for said containers and a hopper device, wherein said interfacing apparatus comprises said capsules arriving from said pneumatic mail system, each of said capsules comprising an upper flange and a lower flange separably mounted on said capsule suitable for passing an inner chamber of said capsule from a closed position, suitable for withholding in sealing manner said biological product containers inside the inner chamber of the capsule, to an opened position, suitable for opening said inner chamber of the capsule by moving vertically a piston of said transfer device to engage said lower flange and transporting said lower flange to a lower position of said piston where transferring means of said transfer device being suitable for transferring said biological product containers to a selected of at least two cavities of said surface according to an information provided by a Laboratory Information System of said laboratory automation system and each one of said at least two cavities of said surface being connected to respective at least one of at least two said hopper devices suitable for supplying said biological product containers to said laboratory automation system.

2. The apparatus according to claim 1, wherein said transferring means comprising a tube being on said lower position of said piston where said biological product containers being leveled with said surface and said tube sliding horizontally between said at least two cavities (16a, 16b) of said surface.

3. The apparatus according to claim 2, wherein a lower edge of the tube rests on the surface, which said surface comprising at least three cavities, a central cavity sized suitable for allowing the passage of the lower flange, and said at least two cavities being side and being of possibly irregular shape but of width at least equal to the diameter of the tube.

4. The apparatus according to claim 1, wherein said transferring means of transfer device comprising a rotatable tube being on said lower position of said piston, said rotatable tube suitable for mounting integral said lower flange) of said capsule and said rotatable tube suitable for rotating said capsule to unload the biological product containers from the top of the capsule into a selected of said at least two cavities of said surface.

5. The apparatus according to claim 4, wherein it comprises motor means adapted to reverse the direction of rotation of the rotatable tube.

6. The apparatus according to claim 4, wherein the rotatable tube is rotational essentially by 135° in either one or the other direction with respect to a vertical rest direction.

7. The apparatus according to claim 4 wherein it includes two arc-of-circumference-shaped partitions to prevent the escape of the biological product containers during the rotation of the rotatable tube.

\* \* \* \* \*